United States Patent [19]

Kopietz et al.

[11] Patent Number: 5,455,346

[45] Date of Patent: Oct. 3, 1995

[54] OBTAINING CAPROLACTAM BY CLEAVAGE OF MOLTEN POLYCAPROLACTAM

[75] Inventors: Michael Kopietz, Grünstadt; Ulrich Kalck, Neuhofen; Simon Jones, Leimen; Peter Bassler, Viernheim; Claus-Ulrich Priester, Ludwigshafen, all of Germany

[73] Assignee: BASF Aktiengesellschaft, Ludwigshafen, Germany

[21] Appl. No.: 355,283

[22] Filed: Dec. 12, 1994

[51] Int. Cl.⁶ .................................................. C07D 201/12
[52] U.S. Cl. ...................... 540/540; 540/535; 564/498; 564/488; 562/593; 562/483; 562/487; 562/485
[58] Field of Search ............................................. 540/540

[56] References Cited

U.S. PATENT DOCUMENTS 5,359,061  10/1994  Evans et al. ............................ 540/540

Primary Examiner—Robert T. Bond
Attorney, Agent, or Firm—Keil & Weinkauf

[57] ABSTRACT

Caprolactam is obtained from mixtures which contain polymers or thermoplastic molding materials having the repeating unit

—[—N(H)—(CH$_2$)$_5$—C(O)—]—

(a) by cleavage at elevated temperatures in the presence of a base under reduced pressure or (b) in the presence of water, by using a mixture essentially comprising from 50 to 99.9% by weight of a polymer or of a thermoplastic molding material having the repeating unit

—[—N(H)—(CH$_2$)$_5$—C(O)—]— from 0.1 to 50% by weight of additives selected from the group consisting of inorganic fillers, organic and inorganic pigments and dyes, from 0 to 10% by weight of organic and/or inorganic additives, from 0 to 40% by weight of non-polyamide-containing polymers and from 0 to 20% by weight of polyamides, with the exception of polycaprolactam and copolyamides prepared from caprolactam, and carrying out the cleavage in the presence of a base under reduced pressure, the water content of the mixture used being not more than 0.01% by weight, or carrying out the cleavage in the presence of water without the addition of acid or base at from 270° to 350° C. and a weight ratio of water to polymer or thermoplastic molding material of from 1:1 to 20:1 and in a reaction time of less than 3 hours.

1 Claim, No Drawings

OBTAINING CAPROLACTAM BY CLEAVAGE OF MOLTEN POLYCAPROLACTAM

The present invention relates to processes for obtaining caprolactam from mixtures which contain polymers or thermoplastic molding materials having the repeating unit

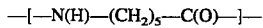

(a) by cleavage at elevated temperatures in the presence of a base under reduced pressure or (b) in the presence of water.

The present invention furthermore relates to the use of the novel process for recycling polycaprolactam-containing wastes.

J. Appl. P. Sci. 22 (1978), 361–368 describes the cleavage of polycaprolactam (PA 6) in the presence of bases under reduced pressure. However, the yield of 90.5% is insufficient for large-scale industrial and economical use.

Furthermore, for example, JP 50131979 and JP 551002 disclose processes for cleaving PA 6 which operate under reduced pressure in the presence of acids. However, in these cases too, the yields of 89 and 69%, respectively, are too unsatisfactory for economical use. Moreover, only the depolymerization of pure polycaprolactam is described.

It is an object of the present invention to provide a process for obtaining caprolactam from polymers and thermoplastic molding materials which gives high yields of caprolactam. It is also intended to provide a process which makes it possible to utilize polycaprolactam-containing wastes which contain inorganic fillers to give caprolactam, without having to accept reduced yields.

We have found that this object is achieved by a process for obtaining caprolactam from mixtures which contain polymers or thermoplastic molding materials having the repeating unit

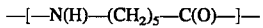

(a) by cleavage at elevated temperatures in the presence of a base under reduced pressure or (b) in the presence of water, by using a mixture essentially comprising
- from 50 to 99.9 % by weight of a polymer or of a thermoplastic molding material having the repeating unit

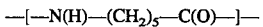

- from 0.1 to 50% by weight of additives selected from the group consisting of inorganic fillers, organic and inorganic pigments and dyes,
- from 0 to 10% by weight of organic and/or inorganic additives,
- from 0 to 40% by weight of non-polyamide-containing polymers and
- from 0 to 20% by weight of polyamides, with the exception of polycaprolactam and copolyamides prepared from caprolactam, and carrying out the cleavage in the presence of a base under reduced pressure, the water content of the mixture used being not more than 0.01% by weight, or carrying out the cleavage in the presence of water without the addition of acid or base at from 270° to 350° C. and a weight ratio of water to polymer or thermoplastic molding material of from 1:1 to 20:1 and in a reaction time of less than 3 hours.

We have also found the use of the novel process for recycling polycaprolactam-containing wastes.

According to the invention, the starting materials used are mixtures consisting essentially of
- from 50 to 99.9, preferably from 60 to 99.9,% by weight of a polymer or of a thermoplastic molding material having the repeating unit

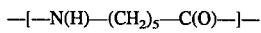

- from 0.1 to 50, preferably from 0.1 to 40,% by weight of additives selected from the group consisting of inorganic fillers, organic and inorganic pigments and dyes,
- from 0 to 10, preferably from 0 to 5,% by weight of organic and/or inorganic additives,
- from 0 to 40, preferably from 0 to 20,% by weight of non-polyamide-containing polymers and
- from 0 to 20, preferably from 0 to 15,% by weight of polyamides, with the exception of polycaprolactam and copolyamides prepared from caprolactam.

A preferably used polymer is polycaprolactam having a relative viscosity of, preferably, from 1.5 to 5.0, particularly preferably from 2.0 to 4.0 (measured at a concentration of 1 g of polymer per 100 ml in 96% strength by weight sulfuric acid at 25° C.). It is of course also possible to use polycaprolactam which contains oligomers in an amount of from 0.01 to 10, preferably from 0.05 to 0.5, % by weight, based on the total amount.

It is also possible to use copolyamides obtained from caprolactam and other polyamide-forming monomers, for examples salts formed from a dicarboxylic acid, such as adipic acid, sebacic acid and terephthalic acid, and a diamine, such as hexamethylenediamine and tetramethylenediamine, preferably AH salt (obtained from adipic acid and hexamethylenediamine), and lactams, such as laurolactam.

Observations to date have shown that all known polycaprolactams can be converted into caprolactam by the novel process, for example also a polycaprolactam which was prepared in the presence of mono- or dicarboxylic acids or amines, which act as chain regulators, for example acetic acid, propionic acid, benzoic acid, hexamethylenediamine, $C_4$-$C_{10}$-alkanedicarboxylic acids, such as adipic acid, pimelic acid, suberic acid, azelaic acid, sebacic acid, undecanedioic acid, dodecanedioic acid and mixtures thereof, $C_5$-$C_8$-cycloalkanedicarboxylic acids, such as cyclopentane- 1,3-dicarboxylic acid, cyclohexane-1,4-dicarboxylic acid and mixtures thereof, benzene- and naphthalenedicarboxylic acids which may carry up to two sulfo groups, including the corresponding alkali metal salts, and whose carboxyl groups are not adjacent, such as terephthalic acid, isophthalic acid and naphthalene-2,6-dicarboxylic acid, 5-sulfoisophthalic acid and its sodium and lithium salts, and mixtures thereof, and 1,4-piperazinedi-$C_1$-$C_6$-alkanedicarboxylic acids, such as 1,4-piperazinediacetic acid, 1,4-piperazinedipropionic acid, 1,4-piperazinedibutyric acid, 1,4-piperazinedipentanoic acid and 1,4-piperazinedihexanoic acid.

Corresponding copolyamides are known to a person skilled in the art and can be prepared by processes which are described, for example, in WO 93/25736, DE-A 14 95 198 and DE-A 25 58 480.

Observations to date have shown that all fillers, such as glass fibers, calcium carbonate and talc, which are usually used in the compounding of polyamides may be employed as inorganic fillers. Observations to date have shown that suitable inorganic and organic pigments and dyes are all pigments and dyes, such as titanium dioxide, iron oxides and carbon blacks, which are usually used for coloring polyamides, and the conventional spinning dyes, such as chromium complexes or copper complexes.

Conventional stabilizers and antioxidants, heat stabilizers and UV stabilizers, antistatic agents and flameproofing agents may be used as organic and inorganic additives.

Antioxidants and heat stabilizers are, for example, sterically hindered phenols, hydroquinones, phosphites and derivatives and substituted members of this group and mixtures of these compounds, as well as copper compounds, such as copper(I) iodide and copper(II) acetate.

Examples of UV stabilizers are substituted resorcinols, salicylates, benzotriazoles, benzophenones and compounds of the HALS (hindered amine light stabilizer) type, and manganese(II) compounds are also suitable for this purpose.

The conventional substances, for example poly(alkylene oxides) and derivatives thereof, may be used as antistatic agents. The conventional chlorine- and nitrogen-containing compounds, such as melamine cyanurate and aluminum hydroxide as well as 1,2,3,4,7,8,9,10,13,13,14,14-dodecachloro-1,4,4a,5,6,6a,7,- 10,10a,11,12,12a-dodecahydro-1,4:7,10-dimethanodibenzo[a,e]cyclooctene (Diels-Alder product of hexachlorocyclopentadiene and 1,5-cyclooctadiene and commercially available under the name Dechlorane®), may be used as flameproofing agents.

The conventional thermoplastic engineering polymers, such as polymers based on ethylene, propylene and styrene, and copolymers thereof with butadiene may be used as non-polyamide-containing polymers.

Suitable polyamides with the exception of polycaprolactam and copolyamides prepared from caprolactam are, for example, polyamide 66, polyamide 610 and polyamide 46.

Preferred starting materials are polycaprolactam which contains inorganic fillers, in particular glass fibers, and is to be disposed of or wastes which are obtained in the production of polycaprolactam and the processing thereof to give filaments, films or injection molded or extruded parts, and shaped utility articles, such as films, packaging, fabric, carpet fibers, carpeting, filaments and extruded parts, which are to be disposed of.

According to the invention, the cleavage in variant (a) is carried out in the presence of a base at from 0.01 to 10, preferably from 0.1 to 2.5, kPa, the water content of the mixture used being not more than 0.01% by weight.

The temperature in the melt is chosen as a rule in the range from 240° to 350° C., preferably 250° to 310° C.

According to the invention, the base used is a compound selected from the group consisting of alkali metal oxide, alkali metal hydroxide, alkali metal carbonate, alkali metal alcoholate, alkaline earth metal oxide, alkaline earth metal hydroxide and alkaline earth metal carbonate, such as sodium oxide, potassium oxide, magnesium oxide, calcium oxide, sodium hydroxide, potassium hydroxide, calcium hydroxide, sodium carbonate, potassium carbonate, sodium methylate, calcium carbonate or magnesium carbonate, preferably sodium hydroxide, potassium hydroxide or a mixture of sodium hydroxide and potassium hydroxide.

The amount of base depends essentially on the basicity of the base to be used and is from 0.1 to 100, preferably from 0.5 to 30, g per kg of polycaprolactam or polycaprolactam-donating polymer used, for example when sodium hydroxide and potassium hydroxide are employed.

In the procedure in an autoclave, the reaction time is usually from 0.25 to 6, preferably from 0.5 to 3, hours.

In variant (b), the mixture used is heated with up to a 20-fold excess of water to 270°–350° C., preferably 280°–330° C. at from 80 to 150, preferably from 100 to 120 kPa, the weight ratio of water to polymer in the mixture used being chosen in the range from 1:1 to 20:1, preferably from 7:1 to 10:1, and no acid or base being added.

The reaction time is usually from 0.25 to 5, preferably from 0.75 to 1.5, hours.

After the cleavage, the reaction mixture can be worked up in the usual manner, for example by filtering off or decanting the insoluble components, such as glass fibers, pigments, etc., and obtaining caprolactam from the filtrate, preferably by distillation.

The caprolactam obtained according to the invention is preferably fed to a purification stage for caprolactam which is used in the preparation of caprolactam. Further possibilities for, if desired, purifying the caprolactam obtained according to the invention are disclosed, for example, in EP-A 568,882 and 570,843. The purified caprolactam is then available in general for further use, in particular for the preparation of PA 6.

The novel process can be used for recycling polycaprolactam-containing wastes, such as used carpets, carpet offcuts, plastics parts, fibers, aqueous extracts and oligomers.

The advantages of the novel process over prior art processes are the cleavage yields of up to 93%, short residence times and smaller amounts of wastes requiring treatment and disposal.

EXAMPLES

Example 1

In a 1 l autoclave, 250 g of polyamide 6 (Ultramid® BS 400 (BASF), relative viscosity=2.4 (measured at a concentration of 1 g of polymer per 100 ml in 96% strength by weight sulfuric acid at 25° C.), having a residual moisture content of 0.01% by weight) and 5.0 g of sodium hydroxide were heated to 280° C. at 20 kPa. After a reaction time of 2 hours, 231.9 g of caprolactam were obtained from the reaction mixture by distillation. Yield: 93%.

Examples 2 to 9

Various PA 6-containing polymers were subjected to the alkaline cleavage similarly to Example 1. The mixtures used and the yields are shown in Table 1.

TABLE 1

| | Alkaline cleavage | | |
| --- | --- | --- | --- |
| Example | Substance used | Caprolactam [g] | Yield [%] |
| 1 | Polycaprolactam containing 36% by weight of glass fibers (Ultramid ® B3G7 (BASF), relative viscosity = 2.7) | 144.3 | 90 |
| 2 | Polycaprolactam containing Dechlorane ® as fireproofing agent and containing 30% by weight of talc (Ultramid ® B3 UM6 (BASF), relative viscosity = 2.7) | 137.6 | 79 |
| 3 | Polycaprolactam containing 30.2% by weight of glass fibers Ultramid ® RC 6000 (BASF), relative viscosity = 2.7) | 158.8 | 91 |
| 4 | Polycaprolactam concentrate obtained from carpeting (containing 75% by weight of polycaprolactam)[1] | 171.6 | 92 |
| 5 | Copolyamide 6/66 (prepared from ≈85% by weight of caprolactam and | 195.4 | 92 |

TABLE 1-continued

Alkaline cleavage

| Example | Substance used | Caprolactam [g] | Yield [%] |
|---|---|---|---|
| | 15% by weight of AH salt, Ultramid ® C S5, relative viscosity = 3.25) | | |
| 6 | Blend of PA 6 and PA 66 (in weight ratio of 80:20; relative viscosity = 2.7 in each case) | 182.2 | 91 |
| 7 | Polycaprolactam (propionic acid-regulated; Ultramid ® BS 400 (BASF), relative viscosity = 2.4) | 231.9 | 93 |
| 8 | Polycaprolactam (propionic acid-regulated; Ultramid ® BS 700 (BASF), relative viscosity = 2.7) | 232.6 | 93 |
| (comparison) 9 | Polycaprolactam (Ultramid ® BS 3300 (BASF), relative viscosity = 3.3) | 232.8 | 93 |

[1] The carpetings were freed from polyamide-free components until the amount of polycaprolactam was by weight, based on the mixture.

Example 10

In a 1 l autoclave, 40 g of polyamide 6 (Ultramid® BS 400, relative viscosity=2.4) were heated to 310° C. with 400 g of water for 1.5 hours. Caprolactam and aminocaproic acid were then removed from the reaction mixture by distillation. The yield of caprolactam was 74%, that of aminocaproic acid was 8% and that of oligomers was 2%.

Examples 11 to 18

Various PA 6-containing polymers were subjected to the hydrolytic cleavage similarly to Example 10. The mixtures used and the yields are shown in Table 2.

TABLE 2

Hydrolytic cleavage

| Example | Substance used | Caprolactam [g] | Yield [%] |
|---|---|---|---|
| 10 | Polycaprolactam containing 36% by weight of glass fibers (Ultramid ® B3G7 (BASF), relative viscosity = 2.7) | 18.9 | 74 |
| 11 | Polycaprolactam containing Dechlorane ® as fireproofing agent and containing 30% by weight of talc (Ultramid ® B3 UM6 (BASF), relative viscosity = 2.7) | 18.7 | 67 |
| 12 | Polycaprolactam containing 30.2% by weight of glass fibers Ultramid ® RC 6000 (BASF), relative viscosity = 2.7) | 21.0 | 75 |
| 13 | Polycaprolactam concentrate obtained from carpeting (containing 75% by weight of polycaprolactam)[1] | 21.7 | 72 |
| 14 | Copolyamide 6/66 (prepared from 85% by weight of caprolactam and 15% by weight of AH salt, Ultramid ® C 35, relative viscosity = 3.25) | 25.6 | 75 |
| 15 | Blend of PA 6 and PA 66 (in weight ratio of 80:20; relative viscosity = 2.7 in each case) | 22.9 | 72 |
| 16 | Polycaprolactam (propionic acid-regulated; Ultramid ® BS 400 (BASF), relative viscosity = 2.4) | 30.2 | 75.5 |
| 17 | Polycaprolactam (propionic acid-regulated; Ultramid ® BS 700 (BASF), relative viscosity = 2.7) | 29.7 | 74 |
| (Comparison) 18 | Polycaprolactam (Ultramid ® BS 3300 (BASF), relative viscosity = 13.3) | 29.9 | 75 |

[1] The carpetings were freed from polyamide-free components until the amount of polycaprolactam was by weight, based on the mixture.

Example 19

(Cleavage with Phosphoric Acid)

In a 1 l autoclave, 250 g of polyamide 6 (Ultramid® BS 700, relative viscosity=2.7) were heated to 265° C. with 12.5 g of 85% strength by weight phosphoric acid. Steam heated to 360° C. was then passed through the resulting melt. A 25% strength by weight caprolactam solution was obtained, the caprolactam yield being 222.6 g (89%).

We claim:

1. A process for obtaining caprolactam from mixtures which contain polymers or thermoplastic molding materials having the repeating unit

—[—N(H)—(CH$_2$)$_5$—C(O)—]—

(a) by cleavage at elevated temperatures in the presence of a base under reduced pressure or (b) in the presence of water, which comprises using a mixture essentially comprising from 50 to 99.9% by weight of a polymer or of a thermoplastic molding material having the repeating unit

—[—N(H)—(CH$_2$)$_5$—C(O)—]—

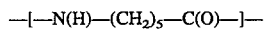

0.1 to 50% by weight of additives selected from the group consisting of inorganic fillers, organic and inorganic pigments and dyes, from 0 to 10% by weight of organic or inorganic additives, from 0 to 40% by weight of non-polyamide-containing polymers and from 0 to 20% by weight of polyamides, with the exception of polycaprolactam and copolyamides prepared from caprolactam, and carrying out the cleavage in the presence of a base under reduced pressure, the water content of the mixture used being not more than 0.01% by weight, or carrying out the cleavage in the presence of water without the addition of acid or base at from 270° to 350° C. and a weight ratio of water to polymer or thermoplastic molding material of from 1:1 to 20:1 and in a reaction time of less than 3 hours.

* * * * *

REEXAMINATION CERTIFICATE (3728th)

United States Patent [19]

Kopietz et al.

[11] B1 5,455,346

[45] Certificate Issued Feb. 9, 1999

[54] OBTAINING CAPROLACTAM BY CLEAVAGE OF MOLTEN POLYCAPROLACTAM

[75] Inventors: Michael Kopietz, Grünstadt; Ulrich Kalck, Neuhofen; Simon Jones, Leimen; Peter Bassler, Viernheim; Claus-Ulrich Priester, Ludwigshafen, all of Germany

[73] Assignee: BASF Corporation, Mt. Olive, N.J.

Reexamination Request:
No. 90/004,976, Apr. 27, 1998

Reexamination Certificate for:
Patent No.: 5,455,346
Issued: Oct. 3, 1995
Appl. No.: 355,283
Filed: Dec. 12, 1994

[51] Int. Cl.[6] ................................................. C07D 201/12
[52] U.S. Cl. ..................... 540/540; 540/535; 562/483; 562/485; 562/487; 562/593; 564/488; 564/498
[58] Field of Search ........................ 540/535, 540; 562/483, 485, 487, 593; 564/488, 498

[56] References Cited

U.S. PATENT DOCUMENTS

| | | | |
|---|---|---|---|
| 5,233,037 | 8/1993 | Nielinger et al. | 540/540 |
| 5,359,062 | 10/1994 | Fuchs et al. | 540/540 |
| 5,359,601 | 10/1994 | Evans et al. | 540/540 |

FOREIGN PATENT DOCUMENTS

| | | |
|---|---|---|
| 851194 | 10/1952 | Germany . |
| S54-21353 | 7/1979 | Japan . |

OTHER PUBLICATIONS

A.K. Mukherjee and D.K. Goel, Polymerization of Poly-e–caprolactam Catalyzed by Sodium Hydroxide, Journal of Applied Polymer Science, vol. 22, pp., 361–368 (1978).

WPI/Derwent Abstract 75–53048W for Japanese Patent JP A 50035183 (1979).

*Primary Examiner*—Richard L. Raymond

[57] ABSTRACT

Caprolactam is obtained from mixtures which contain polymers or thermoplastic molding materials having the repeating unit

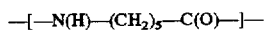

(a) by cleavage at elevated temperatures in the presence of a base under reduced pressure or (b) in the presence of water, by using a mixture essentially comprising from 50 to 99.9% by weight of a polymer or of a thermoplastic molding material having the repeating unit

from 0.1 to 50% by weight of additives selected from the group consisting of inorganic fillers, organic and inorganic pigments and dyes, from 0 to 10% by weight of organic and/or inorganic additives, from 0 to 40% by weight of non-polyamide-containing polymers and from 0 to 20% by weight of polyamides, with the exception of polycaprolactam and copolyamides prepared from caprolactam, and carrying out the cleavage in the presence of a base under reduced pressure, the water content of the mixture used being not more than 0.01% by weight, or carrying out the cleavage in the presence of water without the addition of acid or base at from 270° to 350° C. and a weight ratio of water to polymer or thermoplastic molding material of from 1:1 to 20:1 and in a reaction time of less than 3 hours.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

1. A process for obtaining caprolactam from mixtures which contain polymers or thermoplastic molding materials having the repeating unit

[(a) by cleavage at elevated temperatures in the presence of a base under reduced pressure or (b)] *by cleavage* in the presence of water, which comprises using a mixture essentially comprising from 50 to 99.9% by weight of a polymer or of a thermoplastic molding material having the repeating unit

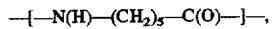

0.1 to 50% by weight of additives selected from the group consisting of inorganic fillers, organic and inorganic pigments and dyes, from 0 to 10% by weight of organic or inorganic additives, from 0 to 40% by weight of non-polyamide-containing polymers, and from 0 to 20% by weight of polyamides, with the exception of polycaprolactam and copolyamides prepared from caprolactam, and [carrying out the cleavage in the presence of a base under reduced pressure, the water content of the mixture used being not more than 0.01% by weight, or] *carrying out the cleavage in the presence of water without the addition of acid or base at from 270° to 350° C. and a weight ratio of water to polymer or thermoplastic molding material of from 1:1 to 20:1 and in a reaction time of less than 3 hours.*

* * * * *